United States Patent [19]

Wiita et al.

[11] Patent Number: 4,772,276
[45] Date of Patent: Sep. 20, 1988

[54] CATHETER TUBE COUPLING ASSEMBLY AND METHODS

[75] Inventors: Thomas A. Wiita; Harvey R. Moorehead, both of Salt Lake City; Karl L. Schatten, Murray, all of Utah

[73] Assignee: Catheter Technology Corp., Salt Lake City, Utah

[21] Appl. No.: 78,431

[22] Filed: Jul. 27, 1987

Related U.S. Application Data

[63] Continuation of Ser. No. 64,277, Jun. 18, 1987.

[51] Int. Cl.$^4$ ............................................. A61N 25/00
[52] U.S. Cl. ...................................... 604/283; 604/905
[58] Field of Search ................ 604/93, 175, 183, 283, 604/DIG. 905, 891; 285/239, 242; 128/1 R

[56] References Cited

U.S. PATENT DOCUMENTS

| | | | |
|---|---|---|---|
| 3,042,045 | 7/1962 | Sheridan | 604/283 |
| 3,217,710 | 11/1965 | Beall et al. | 604/905 |
| 3,310,051 | 3/1967 | Schulte | |
| 3,315,986 | 4/1967 | Quick | 285/242 |
| 3,515,124 | 6/1970 | Gurchot | 604/175 |
| 4,313,629 | 2/1982 | Winterhalter | 285/242 |
| 4,405,319 | 9/1983 | Cosentino | 604/175 |
| 4,464,178 | 8/1984 | Dalton | 604/174 |
| 4,496,350 | 1/1985 | Cosentino | 604/175 |
| 4,569,675 | 2/1986 | Prosl et al. | 604/175 |
| 4,578,063 | 3/1986 | Inman et al. | 604/175 |
| 4,588,402 | 5/1986 | Igari et al. | 604/408 |
| 4,632,671 | 12/1986 | Dalton | 604/174 |
| 4,634,422 | 1/1987 | Kantrowitz et al. | 604/175 |
| 4,641,860 | 2/1987 | McMickle et al. | 285/242 |
| 4,673,394 | 6/1987 | Fenton, Jr. et al. | 604/175 |
| 4,704,103 | 11/1987 | Stöber et al. | 604/175 |

OTHER PUBLICATIONS

Implantofix Literature.
Gish Biomedical, Inc. Literature.

*Primary Examiner*—John D. Yasko
*Attorney, Agent, or Firm*—Lynn G. Foster

[57] ABSTRACT

A port/catheter tube assembly which insures a stable essentially inseparable connection between the hollow male outlet stem of the port and the proximal end of the catheter tube, thereby insuring a continual supply of medication to the desired patient site while preventing inadvertent harm caused by unintended leakage of such medication into improper tissue sites due to separation of the catheter tube from the port or due to kinking.

2 Claims, 1 Drawing Sheet

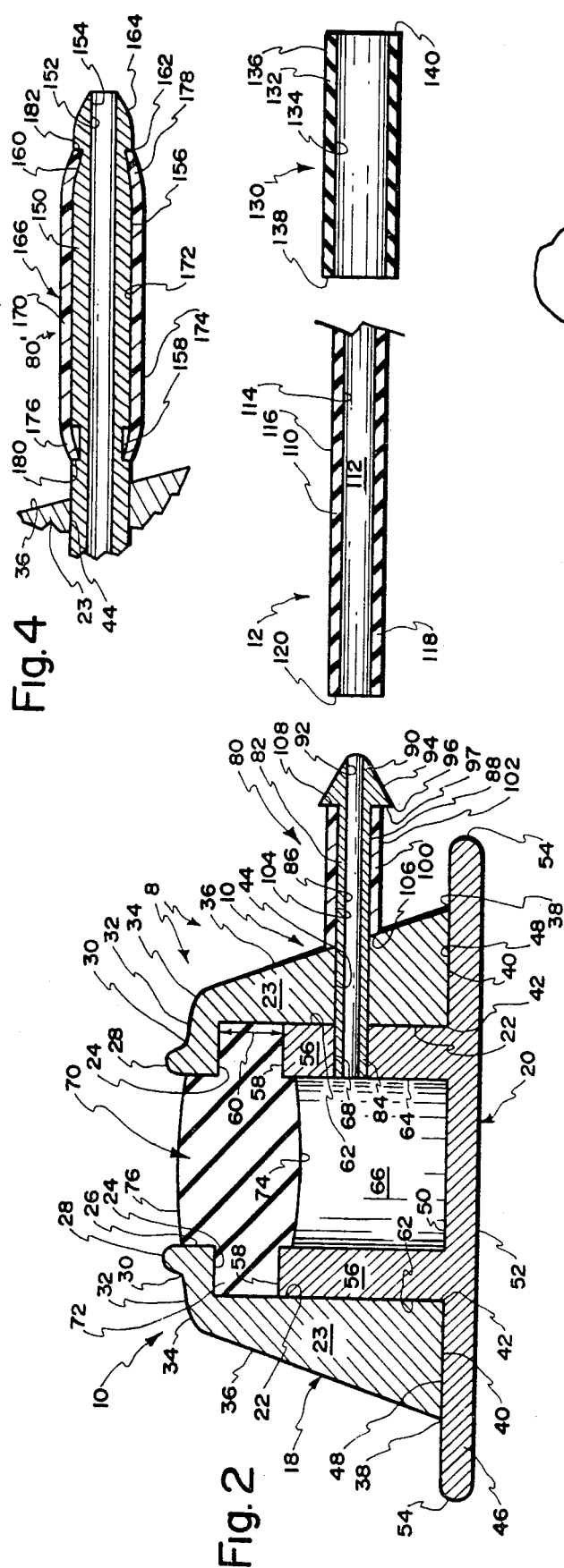
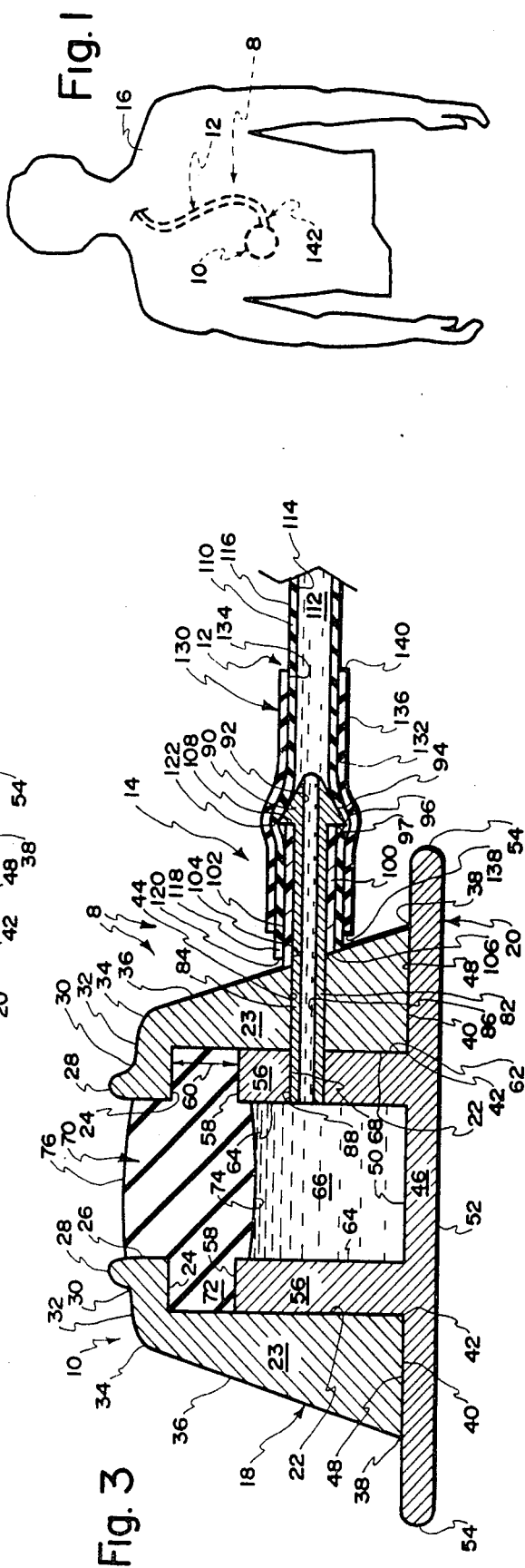

CATHETER TUBE COUPLING ASSEMBLY AND METHODS

This application is a continuation of our co-pending U.S. patent application Ser. No. 64,277, filed June 18, 1987, now pending.

FIELD OF INVENTION

The present invention relates generally to subcutaneous placement of a port/catheter tube assembly and more particularly to a novel, easily assembled port/catheter tube connector which prevents the catheter tube from being pulled off, blown off with internal pressure in the assembly, or otherwise inadvertently separated from a hollow male stem of the port, while providing strain relief.

PRIOR ART

Some medical treatments, such as chemotherapy, require repeated introduction of chemical substances into a patient's body. Often, these chemical substances are introduced into a specific body site. Earlier, it was typical for such chemicals to be introduced by intravenous injection through the patient's skin into a vein. However, such repeated venipuncture injections are painful and often difficult, especially with elderly patients. Newer chemotherapy agents are highly reactive and so traumatic to small peripheral veins that the veins cannot tolerate multiple injections. Also, such intravenous injections are often undesirable because the need for controlled long term introduction cannot be attained. For example, longer term time-release introduction of the chemicals cannot be achieved using a syringe with a hypodermic needle directly in a vein. An IV tube and bottle undesirably results in patient immobility, among other things.

To address the aforementioned deficiencies, implantable infusate injection ports have been developed. These injection ports include an internal chamber, a penetrable self-sealing septum and a hollow male outlet stem, and are implanted subcutaneously within the patient, typically at a chest site. At the time of implantation of the port, a catheter tube is also implanted, with the distal or leading end placed at the desired body site and the proximal or trailing end coupled to hollow male stem in fluid communicating relation. Such a port provides a permanent injection site without immobilizing the patient. The implant port and catheter tube assembly remain in constant fluid communication with the specific body site selected for introduction of the desired chemical. Thus, many prior problems associated with direct injection into veins, arteries and other body cavities have been resolved. Serious problems, however, remain with the use of previously proposed implantable port/catheter tube assemblies.

Once the port/catheter tube assembly is implanted under the skin, any deficiencies associated therewith cannot be readily detected. The most serious problem is inadvertent, undetected separation of the proximal end of the catheter tube from the hollow male stem of the port. This sometimes occurs, for example, when the catheter tube is inadvertently pulled off of the port outlet by movement of the patient or when the catheter tube is blown off of the outlet due to internal pressure created during the injection of a chemical into the chamber of the port. When this occurs, the chemical within the port leaks out into the surrounding body tissue. This can and normally does cause severe problems, especially with highly toxic substances such as those used in chemotherapy. Since such a loss of connection cannot be immediately visually detected, severe injury to the patient often results before any preventive steps can be taken.

Another problem occurs when the catheter becomes kinked or otherwise damaged at the port/catheter tube connection site. Because the port outlet is generally constructed of a more rigid material than is the catheter tube, the catheter tube has a tendency to occlude due to kinking at the connection site. When this occurs, not only is the patient's drug supply cut off, but also high internal pressures are produced within the port chamber at the next injection of medication, which may cause the aforementioned separation of the proximal end of the catheter tube from the port outlet stem causing the problem identified above. In addition, kinking of the catheter tube causes a weakening thereof which can also result in leakage of the strong medication into the tissue adjacent the kink.

There are several prior art port/catheter tube assemblies on the market. Commercial prior art port/catheter tube assemblies may be divided into two types, i.e. those wherein the proximal end of the catheter tube is connected to the male outlet stem of the port and those wherein said connection is made at the time of surgical placement. The factory connections is typically done by gluing the catheter tube to the port, or insert-molding it to a stem on the port, or connecting it with an interference fit, e.g. suturing it on, and then covering up the connection with a molded or glued on cosmetic cover. The physician, at the time of surgical placement, trims the catheter tube to length at the distal tip, the places it at the desired body site. This method has disadvantages because the proper length must be estimated by laying the catheter tube out on the patient's chest prior to insertion and the catheter tube trimmed to length at that time. Once the distal end of the catheter has been placed in the body, the actual location can be checked via X-ray, but the option of further trimming is no longer available. Instead, the position of the catheter tube must thereafter be adjusted by lengthening the subcutaneous pocket where the port is to be placed, thereby increasing tissue trauma for the patient.

Where the port-to-catheter tube connection is made at the time of surgical placement, two prior art techniques are used. One technique is to place a fitting at the proximal end of the catheter tube at the factory. This approach has the advantage that the proximal end fitting on the catheter tube can be designed to provide an easy-to-use, secure connection to the port. This also has the advantage that the catheter tube and the port can be handled separately during placement. Thus the catheter tube can be placed and the port can be sewn into its subcutaneous pocket as separate items, and then connected as the last step before closing the skin. This offers superior convenience to the glued-on connection. However, it still carries the serious drawback that the catheter tube must be trimmed to length at the distal end prior to placement.

The other technique used to connect the proximal end of the catheter tube to the male stem of the port does not use a fitting preattached to the proximal end of the catheter tube at the factory. The present invention falls into this realm. Simply stated a raw cut is made at the proximal end of the catheter tube to size the catheter tube and said raw end is thereafter connected to the port stem. This method has the advantage that the proximal end catheter tube can be trimmed to length after correct placement of the distal end of the catheter tube has been confirmed by X-ray and adjusted if necessary. Another advantage is that the distal tip can be pre-manufactured at the factory to have an optimal shape that minimizes irritation, thrombus-formation, etc.

However, the raw cut end left on prior catheter tubes when cut to length at the proximal end during surgical placement is also a potential source of clotting due to turbulence-producing irregularities left on the tip during cutting. A further disadvantage has been the tendency of the raw end connections of the prior art to inadvertently separate from the port after surgical placement.

Applicant is also aware of the following U.S. Patents, which are of general interest only:

U.S. Pat. Nos. 3,310,051; 4,578,063; 4,464,178; 4,632,671; 4,569,675; 4,634,422.

With the foregoing in mind, prior art implantable injection ports, while solving many prior problems, have not been an entirely satisfactory approach, especially to chemotherapy treatments.

BRIEF SUMMARY AND OBJECTS OF THE INVENTION

In brief summary, the present invention comprises a port/catheter assembly and related methods, wherein inadvertent separation of the proximal end of the catheter tube from the male outlet stem after implantation is entirely overcome or substantially alleviated. The present invention, which insures a stable connection, normally made at the time of surgical placement, between the port outlet tube and the proximal end of a catheter tube, is easy to use and patient injury is avoided because the catheter tube is incapable of being blown off or pulled off inadvertently, under conditions incident to normal use.

With the foregoing in mind, it is a principal object of the present invention to provide novel connector structure for a port/catheter tube assembly intended for subcutaneous implantation and related methods.

A further significant object of the present invention is to provide an improved connector, normally made at the time of surgical placement for an implantable port/catheter tube assembly used to internally infuse medication into a patient.

Another primary object of the invention is to provide a novel port/catheter tube connector and related methods which prevent inadvertent disconnection after implantation.

Another important object of the invention is to provide a novel port/catheter tube connector, which eliminates or substantially alleviates harm to a patient resulting from unintended release into the tissue of the patient of medication placed within an internal chamber of the port.

It is a further significant object of the present invention to provide novel connector structure for inseparably connecting the port to the proximal end of a catheter tube to form an implantable port/catheter tube assembly, which substantially prevents occlusion of and damage to the catheter tube due to kinking of the catheter tube at the connection site.

A further object is to provide a novel port/catheter tube connector which is fail safe and may be created facilely.

These and other objects and features of the present invention will be apparent from the detailed description taken with reference to the accompanying drawings.

BRIEF DESCRIPTION OF THE DRAWINGS

FIG. 1 is a schematic view showing the port/catheter tube assembly operatively implanted within a patient;

FIG. 2 is an exploded cross-sectional view of the port/catheter tube assembly of FIG. 1 showing the various parts in their unassembled state;

FIG. 3 is a cross-sectional view similar to FIG. 2 but showing the port/catheter tube assembly in its fully assembled condition; and FIG. 4 is a fragmentary cross-section of another presently preferred stem configuration for the port.

DETAILED DESCRIPTION OF THE ILLUSTRATED EMBODIMENT

Reference is now made to the drawings wherein like numerals are used to designate like parts throughout. More specifically, the present invention is directed toward a port/catheter tube assembly, generally designated 8, shown in its assembled, implanted condition in FIG. 1. The port thereof, generally designated 10, is subcutaneously implanted, typically in the chest region of the patient, with the catheter tube, generally designated 12, connected, at the proximal end thereof, to the port 10 at coupling site 14. As is clear from FIG. 1, the catheter tube is illustrated as being entirely implanted, subcutaneously at the proximal end and central region thereof with the distal end of the catheter tube (not shown) being internally disposed at a desired body location, such as a body cavity or an intravascular or intravenous location.

The port/catheter assembly 8, is more appropriate for the patient 16 than is the use of hypodermic injections or intravenous feedings, where the medication being introduced into a specific body site is required over a protracted period of time and necessitates repetitious introduction of the medication over a prolonged period of time. Use of syringe injections does not accommodate a protracted or time-release introduction of the desired medication (such as the chemicals used in chemotherapy) to the desired body site. Use of intravenous feeding equipment or the like inordinately immobilizes the patient.

Specific reference is now made to FIGS. 2 and 3, which illustrate, in enlarged cross-sectional views, the presently preferred port/catheter assembly 8. FIG. 2 illustrates the parts of the assembly 8 in their disassembled condition, while FIG. 3 illustrates the assembly 8 in its fully assembled condition, with the central portion and distal end of the catheter tube removed for clarity of illustration. The assembly 8 is shown in FIG. 3 as if it were removed from its implanted location depicted in FIG. 1, also for purposes of clarity.

Port 10 is generally dome-shaped and comprises a housing which may be formed from any suitable material, including stainless steel or implantable grades of thermoplastic, titanium being currently the preference of the industry. More specifically, the housing comprises a generally frusto conical housing collar, generally designated 18, and a housing base, generally designated 20.

The collar 18 comprises a tapered wall 23 defining a hollow annular interior at cylindrical surface 22. Cylindrical surface 22 is illustrated as having uniform diameter throughout. Toward the top of the port 10 (as illustrated in FIGS. 2 and 3), the central bore 22 is stepped through two 90 degree angles adjacent each side of shoulder 24 to create a reduced diameter opening at each side of shoulder 24 to create a reduced diameter opening at annular surface 26. Annular surface 26 merges into a rounded upwardly directed flange 28, which projects outwardly from the patient when installed as illustrated in FIG. 1. When subcutaneously implanted, the flange or ring 28 can be readily located by the nurse or the other attendant, under the skin, by use of a finger so that the appropriate injection site for introduction of medication into the port 10 can be readily and accurately located, as hereinafter more fully explained. The rounded flange 28 merges at inside corner 30 along the outside of the port with an annular rounded surface 32, which in turn merges at outside corner 34 with a downwardly divergently tapered generally annular surface 36. The surface 36 merges with a flat base-engaging surface 40 at acute angular corner 38. Base-engaging surface 40 merges at 90 degree corner 42 with the heretofore described bore surface 22. The wall 23 as well as the bore surface 22 and the tapered surface 36 of the housing member 18 are interrupted by a transverse bore 44. Bore 44 is illustrated as being disposed at a 90 degree angle to the axis of the port 10 and is sized and located to accommodate fluid flow from the interior chamber of the port 10 into the hollow interior of the catheter tube 12, as hereinafter more fully explained.

The base housing member 20 comprises a base wall 46, illustrated as being of uniform thickness and comprising an annular top wall surface 48, a central top circular wall surface 50 and a flat bottom wall surface 52. The base wall 46 may be of any suitable shape along its perimeter, such as rectangular, square, oval or circular and comprises an edge 54, illustrated as being rounded in its configuration, which spans between the base wall surfaces 52 and 48. Suture holes may be provided as desired in the exposed areas of the wall 46.

Integral with the base wall surface 48 is a perpendicularly disposed annular boss 56. Boss 56 has an axial length substantially less than the axial length of the bore surface 22 of the housing 18. The boss 56 terminates in a blunt flat edge 58, illustrated as being parallel to but substantially spaced from the shoulder surface 24 by a predetermined distance identified by arrow 60.

The boss or annular wall 56 is formed as one piece with the base wall 46 in the presently preferred embodiment. Annular wall 56 comprises an outside cylindrical wall surface 62 and an inside annular or cylindrical wall surface 64. Essentially the space within the annular wall surface 64 defines a liquid-receiving reservoir or chamber 66. The annular wall 56 is interrupted by an aperture 68, which is disposed normal to the axis of the port 10 and in alignment with the bore 44 disposed in wall 23 of the housing member 18. Aperture 68 and bore 44 are illustrated as being not only aligned one with the other but as having the same diameter. The boss 56 is sized so that surface 62 thereof is snugly contiguous with the bore surface 22 of the housing member 18. Likewise, the top surface 48 of the base wall member 46 is contiguous with the surface 40 of the housing member 18. By use of a suitable bonding agent, adhesive, by welding or by other suitable connector techniques at the interfaces 62/22 and 48/40, housing members 18 and 20 are integrally joined one to the other.

Port 10 also comprises a diaphragm or septum preferably of silicone rubber or like material, generally designated 70. The septum 70 is generally annular in configuration and is sized and shaped to fit snugly, as illustrated, between the surfaces 24 and 58 at annular ring 72 of the septum 70. Preferably, the ring 72 is compressively placed between the wall surfaces 24 and 58 through distance 60. The flange 72 is also sized and shaped to be contiguous with the surface 26 of the housing member 18 and contiguous along a short distance with the boss surface 64. The septum 70 comprises a downwardly directed convex interior surface 74 which forms the top of the internal medication reservoir 66. The septum 70 also comprises a top convex surface 76 (as viewed in FIGS. 2 and 3). Surface 76 fills the circular opening formed by annular surface 26 within the flange 28.

Simply stated, when the nurse or other medical attendant appropriately desires to introduce a liquid medication into the reservoir 66, a hypodermic needle (with syringe, mechanical pump or drip bottle delivery system attached) is inserted through the septum 70. The attendant next causes delivery of the liquid medication through the needle into the reservoir 66. This process is repeated from time to time over a prolonged interval so that the long term medication requirements of the patient may be met for the treatment indicated. The transverse annular flange 72 of the septum 70, firmly gripped between the surfaces 24 and 58, prevents inadvertent dislodgment of the septum 70 from the remainder of the port 10 when normal forces are imposed thereon, thereby preventing undesired release of the medication from the port 66 into the tissue of the patient adjacent the port implantation site. Certain types of liquid medications are highly toxic to human tissue.

Delivery of the liquid medication from reservoir 66 of the port 10 to the catheter tube 12 and thence to the desired body site is accomplished through a male hollow outlet stem, generally designated 80. The outlet stem 80 is illustrated as being an integral part of the port 10. Stem 80 comprises a hollow tubular member 82, which comprises a tube 84 of uniform hollow inside diameter at surface 86 and uniform outside diameter at surface 88. The outside diameter at surface 88 is illustrated as being substantially the same as the diameters of the heretofore described bore 44 and aligned aperture 68. Preferably the tubular member 82 is formed of stainless steel or titanium and is secured within the bore 44 and aperture 68, as illustrated, by a suitable bonding agent, adhesive, by welding or the like.

The tubular member 82 terminates in an enlarged outside leading end 90, which comprises a discharge orifice 92, a convergently tapered surface 94, an annular barb 96 and a shoulder surface 97. The barb 96 functions to secure collar 100, as explained hereinafter.

The tubular member 82 is illustrated as being surrounded by rigid plastic collar 100. Plastic collar 100 is formed of suitable synthetic resinous material which provides an external gripping surface 102 highly resistant to frictional displacement of other synthetic resinous materials along said surface. Extruded polyurethane and extruded polyvinyl chloride tubing respectively provide such a surface. The collar 100 is illustrated as being of uniform wall thickness spanning between an inside cylindrical surface 104 and the outside cylindrical surface 102. Surface 104 is illustrated as being of a diameter substantially the same as the diameter of the outside surface 88 of the tube 84. The collar 100 terminates in a sloped edge 106 shown to be contiguous with the surface 36 adjacent to the bore 44. Collar 100 also terminates in a blunt edge 108, illustrated as being continguous with annular shoulder surface 97, which together with surface 94 forms barb 96. The cylindrical surface 102 has a diameter which is illustrated as being less than the diameter of the barb 96.

The catheter tube 12, preferably formed of silicone rubber or other soft, highly flexible synthetic resinous material, is illustrated as comprising a cylindrical wall 110 of uniform thickness throughout defining a hollow interior or passageway 112 within cylindrical surface 114. The wall 110 is also defined by the smooth exterior cylindrical surface 116. The proximal end of the catheter tube, at 118, is illustrated as terminating in a blunt edge 120. The distal end of the catheter tube 12 may be of any desired configuration, consistent with conventional practices within the applicable catheter art.

The inside diameter of the catheter tube 12 at wall surface 114 is materially less than the outside diameter 102 of the sleeve 100. At the time of assembly, the proximal end 118 of the catheter tube 12 is axially force-displaced over the barb 96 and along the collar 100 into the position illustrated in FIG. 3 thereby substantially enlarging not only the inside diameter but the outside diameter of the catheter tube 12 as well at the proximal end 118. Thus, the proximal end 118 of the catheter tube 12 is caused to exert a compressive radial pressure upon the stem 80 at the surface 102 of the collar 100. This provides a substantial degree of security to the coupling 14 in and of itself. The anti-displacement surface 102 of the collar 100 firmly and contiguously engages the inside surface 114 of the proximal end 118 of the catheter tube 12 which further provides security against inadvertent removal of the proximal end of the catheter tube 12 from the port 10.

In addition, the illustrated embodiment of the present invention comprises a relatively short sleeve or oversleeve, generally designated 130 (FIG. 2). The length of the sleeve 130 is illustrated as being on the order of twice the length of the collar 100. The sleeve 130, formed of suitable synthetic resinous material, preferably silicone rubber or other soft, highly flexible synthetic resinous substance, is illustrated as comprising an annular or cylindrical wall 132 defined by inside and outside cylindrical surfaces 134 and 136, respectively. The sleeve 130 is illustrated as comprising a blunt proximal edge 138 and a blunt leading edge 140. The diameter at cylindrical surface 134 is selected to be only slightly greater than the diameter of the outside surface 116 of the catheter tube 12, thereby accommodating snug axial displacement of the sleeve 130 along the catheter tube 12 during the assembling process.

When the coupling 14 between the proximal end of the catheter tube 12 and the stem 80 of the port 10 has been completed as heretofore described, the sleeve 130, concentrically disposed along the exterior surface 116 of the catheter tube 12, is manually displaced along the catheter tube 12 to the coupling site 14 and is manually force-displaced over the enlarged proximal end 118 of the catheter tube 12 into the interference fit position illustrated in FIG. 3. Thus, the sleeve 130, at the proximal end thereof has been substantially enlarged and, due to the memory of the material from which the sleeve is formed, exerts a radial compressive pressure against the proximal end 118 of the catheter tube 12 thereby providing further stability and retention to the stable and reliable coupling formed at site 14.

Under normal conditions of use, inadvertent separation of the catheter tube 12 from the port 10 at the coupling site 14 is entirely prevented, safeguarding against toxic introduction of the liquid medication placed from time to time in reservoir 66 into the tissue of the patient and insuring that the medication is properly released at the desired body site in accordance with the treatment indicated for the patient. Thus, the catheter tube is not pulled off the port 10 during movement by the patient and is not blown off by internal pressure which occurs when the reservoir is filled with liquid medication in the manner earlier described.

It is to be appreciated that the connection or coupling at site 14 can be achieved at the factory, if desired. However, the primary aim of the present invention is to accommodate said connection at the time of implantation. If the coupling at site 14 occurs at the factory, then it will be necessary to trim the distal end of the catheter tube during implantation so that the distal end is properly placed at the desired body site. When the coupling at site 14 is accomplished at the time of implantation, which is ordinarily the case, the distal end of the catheter tube is placed in the desired position and the proximal end thereof is trimmed prior to the formation of coupling 14.

Reference is now made to FIG. 4, which illustrates a second presently preferred port stem 80' in accordance with the present invention. The port is otherwise the same as heretofore described. The stem 80' is secured in the bores 44 and 68 as heretofore set forth. The stem 80' comprises an elongated tube 150, illustrated as being formed of corrosion resistant metal, such as stainless steel or titanium. Tube 150 has a uniform internal bore 152, which terminates at an outlet orifice 154. The outside surface 156 of the tube 150 is of uniform diameter, with three exceptions. The exceptions comprise (1) an annular radially directed rectangular notch 158, (2) a frusto conical surface 160, which merges with the back side or shoulder of a transversely directed barb 162, and (3) an external rounded distal tip surface 164, which merges at orifice 154 with the interior wall surface 152 defining the central bore of the tube 150.

The stem 80' also comprises an external collar 166. Collar 166 comprises, in its assembled state as illustrated in FIG. 4, a central wall portion 170 of uniform inside diameter, outside diameter and thickness throughout. The inside diameter is defined by an interior cylindrical surface 172. The outside diameter is defined by an exterior cylindrical surface 174. The diameter of cylindrical surface 172, in the assembled state, is illustrated as being the same as the outside diameter of the tubular wall 150, at surface 156.

The collar 166 also comprises a necked down or constricted proximal end 176 and a necked down or constricted distal end 178. The thickness of the wall-forming collar 166 is illustrated as being substantially uniform from end to end. The diameter of the barb 162 is substantially the same as the outside diameter of the central portion 170 of the collar 166. The depth of the notch 158 is substantially the same as the thickness of the wall of the collar 166. Accordingly, the blunt proximal edge 180 seats substantially within the groove 158 and the blunt distal edge 182 of the collar 166 seats substantially behind the trailing edge or rear shoulder of the barb 162.

It is presently preferred that the collar 166 be extruded polyurethane tubing or, alternatively, extruded polyvinyl chloride tubing. It has been found that such tubing, when subjected to an environment of freon or chlorothene first becomes very pliant and expands and thereafter will shrink as the freon vaporizes. By cutting the collar 166 to length and subjecting it to an environment of freon, the collar 166 may be promptly superimposed in rather loose concentric relation upon the steel tube 150. The proximal and distal ends may be manually shaped into the position illustrated in FIG. 4. As the freon evaporates, the tubing forming the collar 166 will shrink and become substantially rigid. The shrinkage causes the collar 166 to exert a compressive radial pressure upon the steel tube 150, thereby retaining the collar 166 upon the tubing 150 against inadvertent relative movement.

The stem 80', is joined to the heretofore described proximal end 118 of the catheter tube 12 and the sleeve 130 to form a coupling between the port and the catheter tube substantially similar to the coupling 14 heretofore described in conjunction with FIG. 3.

The invention may be embodied in other specific forms without department from the spirit or essential characteristics thereof. The present embodiments, are, therefore to be considered in all respects as illustrative and not restrictive, the scope of the invention being indicated by the appended claims rather than by the foregoing description, and all changes which come within the meaning and range of equivalence of the claims are therefore to be embraced therein.

What is claimed and desired to be secured by U.S. Letters Patent is:

1. A barbless catheter tube coupling assembly comprising:

a first hollow fluid flow-accommodating rigid tubular member comprising an exposed synthetic resinous material comprising an elongated gripping exterior surface highly resistant to frictional displacement of other synthetic materials along said surface and having a predetermined outside maximum transverse dimension;

a catheter tube of synthetic resinous material comprising opposed ends, one end telescopically and compressively contiguously superimposed upon substantially the entirety of the gripping surface and comprising outside and inside stressed transverse dimensions, the inside stressed transverse dimension of the one end of the catheter tube along substantially the entirety of the gripping surface of the tubular member being materially greater than the unstressed inside and outside transverse dimensions of said one end with the stressed inside transverse dimension of the assembled one end of the catheter tube being substantially the same as the outside transverse dimension of the first tubular member;

a relative short flexible sleeve of synthetic resinous material telescopically and compressively contiguously superimposed upon the one end of the catheter tube, the flexible sleeve comprising outside and inside stressed transverse dimensions, the inside and outside flexible sleeve transverse dimensions in the stressed state being materially greater than the unstressed inside and outside transverse dimensions of the sleeve, with the stressed inside transverse dimension of the assembled sleeve being substantially the same as the one end of the catheter tube;

the first tubular member, the enlarged one end of the catheter tube and the enlarged sleeve, when assembled, forming a secure ultra strong coupling, stable against inadvertent separation under normal stress conditions, the one end of the catheter tube imposing a substantial compressive memory stress upon the first tubular member, the sleeve imposing a substantial compressive memory stress upon the one end of the catheter tube and through the enlarged proximal end of the catheter tube upon substantially the entirety of the gripping surface of the stem and the gripping surface substantially restraining the one end of the catheter tube against axial displacement relative to the tubular member;

whereby the one end of the catheter tube is reliably secured to the first tubular member against both axial and blow off separation.

2. A method of making a secure barbless catheter tube coupling comprising the steps of:

providing a first hollow fluid flow-accommodating tubular member comprising an elongated non-slip gripping surface of synthetic resinous material;

force diametrally enlarging one end of a catheter tube, telescopically superimposing said one end upon substantially the entire length of the exterior of the first tubular member and causing the one end of the catheter tube to radially compressively grip and longitudinally anti-displacingly engage substantially the entire length of the non-slip gripping surface at the exterior surface of the first tubular member and further restraining the enlarged one end of the catheter tube;

placing a yieldable sleeve slidably and telescopically upon the catheter tube and force diametrally enlarging the yieldable sleeve and superimposing the enlarged sleeve upon the exterior of the enlarged one end of the catheter tube and causing the enlarged sleeve to radially compressively grip the enlarged one end of the catheter tube and substantially the entirety of the elongated gripping surface of the tubular member through the sleeve.

* * * * *